United States Patent
Zacharopoulos et al.

(10) Patent No.: US 6,895,617 B2
(45) Date of Patent: May 24, 2005

(54) PATIENT SUPPORT SYSTEM AND ELEMENTS THEREOF

(75) Inventors: Nick Zacharopoulos, New City, NY (US); Thomas R. Pherson, Erie, PA (US)

(73) Assignee: Aktina Corp., Congers, NY (US)

( * ) Notice: Subject to any disclaimer, the term of this patent is extended or adjusted under 35 U.S.C. 154(b) by 50 days.

(21) Appl. No.: 10/223,912

(22) Filed: Aug. 20, 2002

(65) Prior Publication Data

US 2004/0034932 A1 Feb. 26, 2004

(51) Int. Cl.[7] ................................................. A61B 5/05
(52) U.S. Cl. ........................ 5/601; 378/209; 600/410
(58) Field of Search ..................... 5/601, 600; 378/209, 378/208; 600/410

(56) References Cited

U.S. PATENT DOCUMENTS

| | | | |
|---|---|---|---|
| 3,700,229 A | 10/1972 | Kurokawa et al. | |
| 3,814,419 A | 6/1974 | Bjorklund et al. | |
| 3,840,221 A | 10/1974 | Hogan | |
| 3,981,492 A | 9/1976 | Hallmann | |
| 4,143,652 A * | 3/1979 | Meier et al. | 600/203 |
| 4,487,523 A * | 12/1984 | Monroe | 403/385 |
| 4,520,800 A * | 6/1985 | Kowalski | 606/243 |
| 4,901,964 A * | 2/1990 | McConnell | 248/231.51 |
| 5,385,119 A | 1/1995 | Tarulli | |
| 5,400,772 A * | 3/1995 | LeVahn et al. | 600/230 |
| 5,452,721 A * | 9/1995 | Hacker | 5/601 |
| 5,531,229 A | 7/1996 | Dean et al. | |
| 5,537,454 A | 7/1996 | Korver, II | |
| 5,566,681 A | 10/1996 | Manwaring et al. | |
| 5,689,545 A * | 11/1997 | Hopkins | 378/206 |
| 5,775,337 A | 7/1998 | Hauger et al. | |
| 5,806,116 A | 9/1998 | Oliver et al. | |
| 5,832,550 A | 11/1998 | Hauger et al. | |
| 5,848,449 A | 12/1998 | Hauger et al. | |
| 5,983,426 A * | 11/1999 | Vanek et al. | 5/601 |
| 6,152,599 A * | 11/2000 | Salter, Jr. | 5/601 |
| 6,161,237 A | 12/2000 | Tang et al. | |
| 6,279,579 B1 | 8/2001 | Riaziat et al. | |
| 6,341,398 B1 * | 1/2002 | Heimbrock et al. | 5/601 |
| 6,493,571 B1 * | 12/2002 | Bis et al. | 5/601 |
| 6,499,158 B1 * | 12/2002 | Easterling | 5/600 |
| 6,671,904 B2 * | 1/2004 | Easterling | 5/601 |

* cited by examiner

*Primary Examiner*—Frederick L. Lagman
(74) *Attorney, Agent, or Firm*—Jones Day

(57) ABSTRACT

A patient support system for medical treatments is disclosed having an attached table section, an exchangeable table section and a fastener for the sections, the fastener including a sleeve, a rod and a cam-lock mechanism. The system also includes an easily operated and precisely located clamp for mounting accessory devices to the top of the table sections. The sections include peripheral channels and ridges which are used by the clamp to make a tight engagement. The channels also are used to form a coordinate number scale so that the patient, clamp and accessory devices may be consistently located time after time for multiple periodic treatments.

20 Claims, 11 Drawing Sheets

PATENT SUPPORT SYSTEM AND ELEMENTS THEREOF

BACKGROUND OF THE INVENTION

1. Field of the Invention

The present invention relates to a patient support system and elements thereof and more particularly to a patient support system for radiotherapy treatment and/or imaging, as well as to a table and clamp thereof, which are flexible, easy to use and effective in operation.

2. Description of the Related Art

Patient support tables are used in the medical field in radiation therapy and CT scanning and for other medical procedures. Often there is a need to accurately and repeatedly position a patient for multiple treatments, especially so for radiation therapy, where there is a need to repeatedly expose a cancerous tumor to radiation on a periodic basis. In addition, patient support tables must not interfere with the radiation being transmitted to the patient during therapy sessions so that radiation can be delivered unobstructed to body extremities. Examples of radiation tables are shown in U.S. Pat. Nos. 5,537,454; 5,806,116, and 6,161,237

BRIEF SUMMARY OF THE INVENTION

The modular patient support system disclosed here offers a number of improvements over existing tables. What is described here is a radiotherapy treatment/imaging patient support system including a base, a patient support table connected to the base, the table having an edge, right and left side peripheral portions and upper and lower peripheral portions where the peripheral portions are spaced away from the edge, location indicia formed on the table along one of the left or right peripheral portions where the indicia is a continuous sequence, and a clamp for mounting on the edge of the table, the clamp having an upper jaw portion with an opening, a lower jaw portion, a shaft allowing the lower jaw portion to pivot relative to the upper jaw portion, a lever having a cam for bearing against the lower jaw portion and causing it to tighten around the table and a transparent element having a hairline where the element is mounted in the opening in the upper jaw. What is also described here is the patient support table with exchangeable sections and the clamp.

There are a number of advantages, features and objects achieved with the present invention which are believed not to be available in earlier related devices. For example, one advantage is that the present invention provides a patient support system which is flexible in the sense that a first section of the patient support system is attached to a base while other exchangeable sections may be connected to the first section depending upon the requirements of the patient and the treatment. For example, one connectable section may have an open middle portion while another section may have open edge portions. The use of any particular connectable section will be a function of the part of the patient's body which is to receive radiation treatment, for example. Regardless of the section used, a number scale is provided that establishes a grid system for repeatability placing a patient's body on the table.

Another object of the present invention is to provide a patient support system which has a consistent number scale along its peripheral portions for offering location coordinates so that a patient may be consistently placed on the support system table at the same location during each session of a treatment sequence. The number scale is placed in elongated recesses for ease of mounting an accessory clamp and for allowing the clamp to be consistently aligned using scale markings. Another feature of the present invention is to provide a patient support system which includes clamps that may be used to mount accessory items to the top of the patient support system. Still another object of the present invention is to provide a patient support system which is simply constructed, easily used, light in weight and very versatile. Yet another feature of the present invention is a clamp which allows easy alignment with scale markings for accurate placement of accessories relative to a patient table.

A more complete understanding of the present invention and other objects, advantages and features thereof will be gained from a consideration of the following description of preferred embodiments read in conjunction with the accompanying drawing provided herein. The preferred embodiments represent examples of the invention which is described here in compliance with Title 35 U.S.C. §112, but the invention itself is defined by the attached claims.

DETAILED DESCRIPTION OF PREFERRED EMBODIMENTS OF THE CLAIMED INVENTION

While the present invention is open to various modifications and alternative constructions, the preferred embodiments shown in the attached drawing figures will be described herein in detail. It is understood, however, that there is no intention to limit the invention to the particular forms or examples disclosed herein. On the contrary, the intention is to cover all modifications, equivalent structures and methods, and alternative constructions falling within the spirit and scope of the invention as expressed in the appended claims, pursuant to Title 35 U.S.C. § 112 ($2^{nd}$ paragraph).

Figure 1:
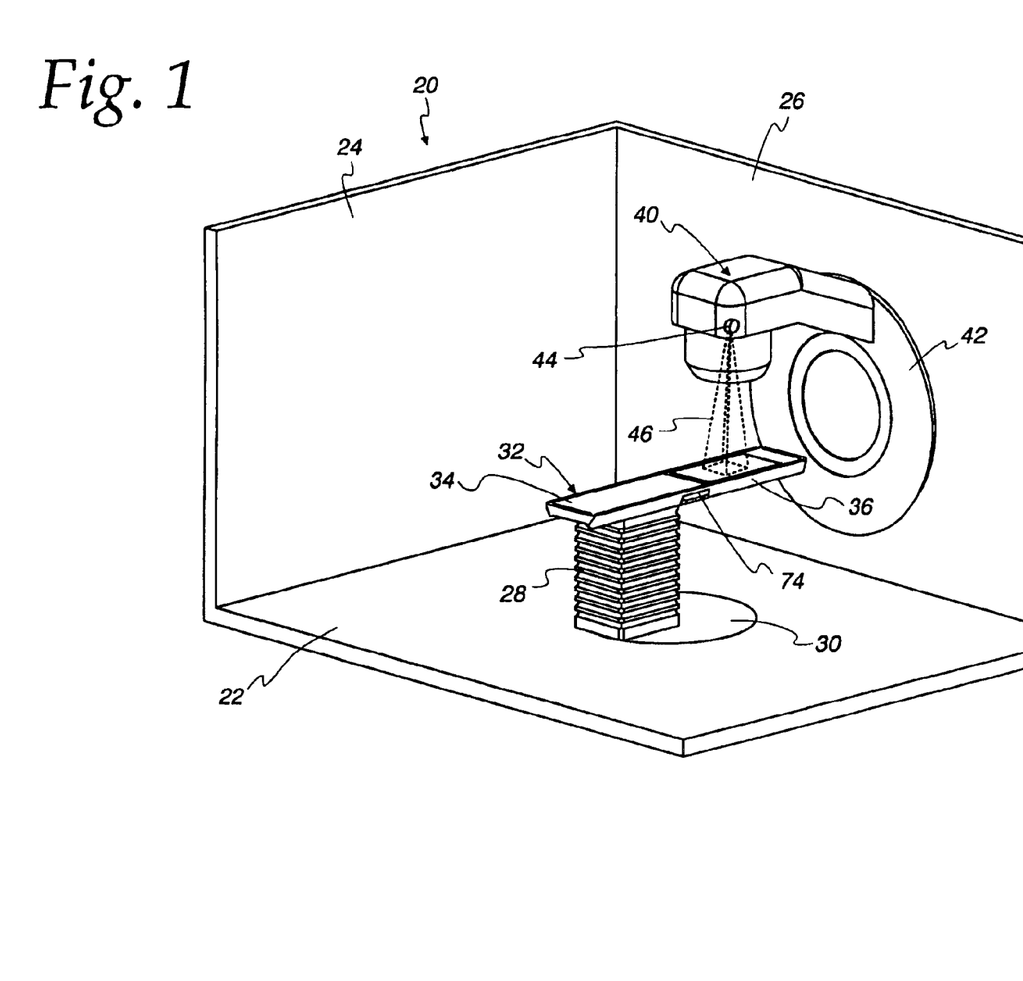
FIG. 1 is a diagrammatic isometric view showing a patient support system in a treatment room.

Referring now to FIG. 1 there is shown in diagrammatic form a treatment room 20 of the type used to practice radiation therapy. The treatment room illustrated includes a floor 22 and two walls 24, 26. The remaining walls and equipment have been removed for purposes of clarity. A base 28 is mounted to a rotating panel 30 which is set into the floor. Attached to the base is a patient support system 32 in the form of a table structure upon which a patient is supported during treatment. The patient support table includes a first or lower patient support section 34 which is attached to the base 28 such as by bolts (not shown), and a second or upper patient support section 36 which is removably connected to the first patient support section to allow section exchanges. The terms "lower" and "upper" when used to describe parts of the table refer to the portions of a patient's body supported by that part of the table. The lower section supports the legs while the upper section supports the upper body and head. It is to be understood that a patient may be placed "up-side-down" if desired, i.e., the legs are supported by the upper section and the upper body is supported by the lower section of the table.

Mounted on the wall 26 is an accelerator treatment head 40 which is attached to a rotating base 42. In addition to relative rotational motion between the treatment head and the patient support system, there is also relative linear motion. Within the treatment head is a radiation source 44 for projecting radiation within a field generally depicted by the dotted lines 46. The patient support system can be moved as can the treatment head 40 so that the treatment head is capable of targeting any portion of a patient's body to be treated.

Figure 2:
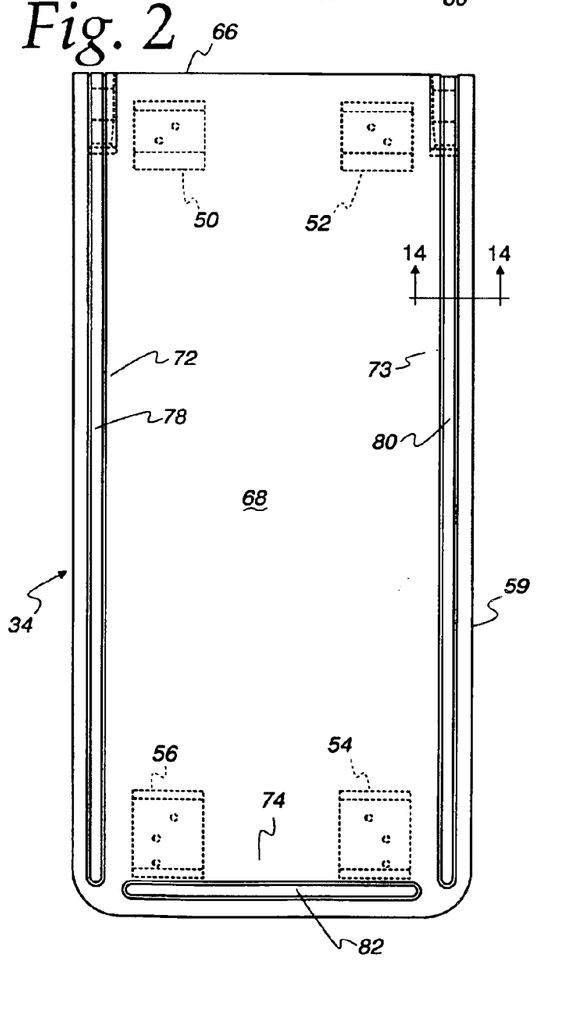
FIG. 2 is a top plan view of a lower section of a patient support table which is adapted to be attached to a base.
Figure 3:
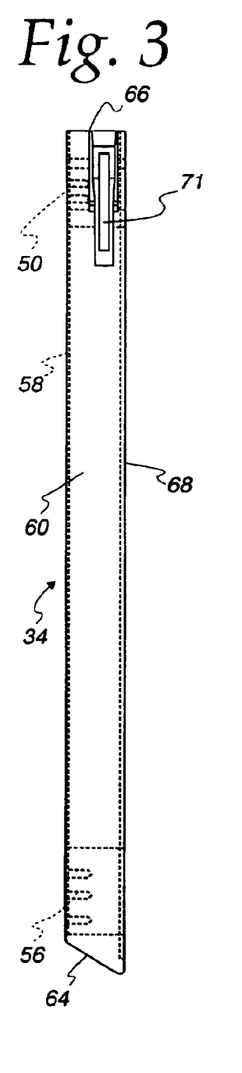
FIG. 3 is a side elevation view of the patient support table section shown in FIG. 2.
Figure 4:
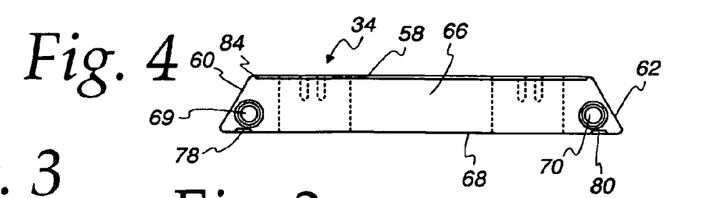
FIG. 4 is a rear elevation view of the patient support table section shown in FIGS. 2 and 3.

Selected sections of the patient support table will next be described in detail. This description will illustrate the flexibility of the system because of modular construction and the ability to easily and simply exchange sections. Further, the simple construction and reliability of the sections will also become evident. Modular tables are already in use in the surgical imaging area. For example, Steris offers a SURGI-GRAPHICS table as does Ohio Medical Instruments and, formally, BETA Medical. Other companies, such as Nucletron, Med-Tec and Varian offer tables with head extensions. Referring now to FIGS. 2–4, the first patient support section 34 is shown in detail. Hereafter the first or lower patient support section may also be called the attached table component (attached to the base 28) whereas the upper, connectable or exchangeable patient support section 36 may be referred to as the exchangeable table component. The attached table component has mounting pads 50, 52, 54, 56 shown in dotted line in FIG. 2 attached to a bottom surface 58. The mounting pads include openings to receive bolts (not shown) that fasten the base 28 to the attached table component. The attached table component has a side edge 59 defined by two slanted side walls 60, 62, a slanted end wall 64 and an oppositely disposed abutment wall 66 intersecting with a top surface 68.

The abutment wall 66 is placed adjacent to a similar wall on the exchangeable table component 36 as will be described hereinbelow. Two fastener sleeves 69, 70 are formed in the abutment wall 66. Adjacent the fastener sleeve 69, 70 in the slanted side walls 60, 62, respectively, are two cam-lock mechanisms of which one such mechanism 71 is shown in FIG. 3.

Figure 5:
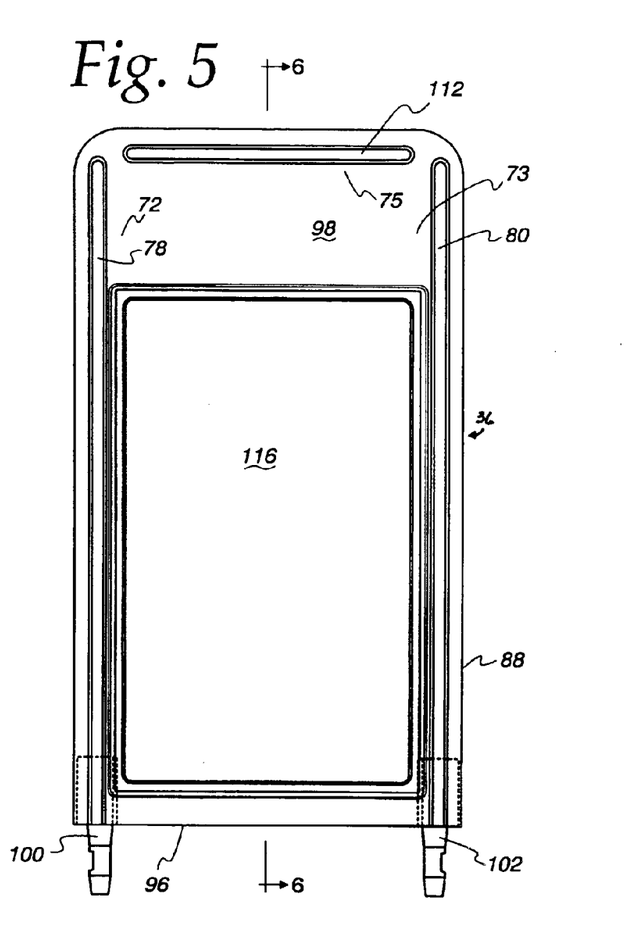
FIG. 5 is a top plan view of one version of a connectable or exchangeable upper section of a patient support table.

The top surface 68 of the attached table component is intended to support a portion of a patient during treatment. The top surface has a left side peripheral portion generally designated by the number 72, a right side peripheral portion generally designated by the number 73 and a lower peripheral portion generally designated by the number 74. An upper peripheral portion generally designated by the number 75 is illustrated in FIG. 5. The peripheral portions are all spaced from the edge 59 of the table. Around the left side peripheral portion 72 of the attached table component is a longitudinally extending left recess or channel 78. A longitudinally extending right recess or channel 80 extends along the right side peripheral portion 73, and a laterally extending recess 82 extends along the lower peripheral portion 74. Along the intersection of the slanted walls and the bottom surface 58 of the table is a downward projecting ridge 84. As will be explained below, the channels and the ridge cooperate with a clamp for attaching accessories to the table.

Figure 6:
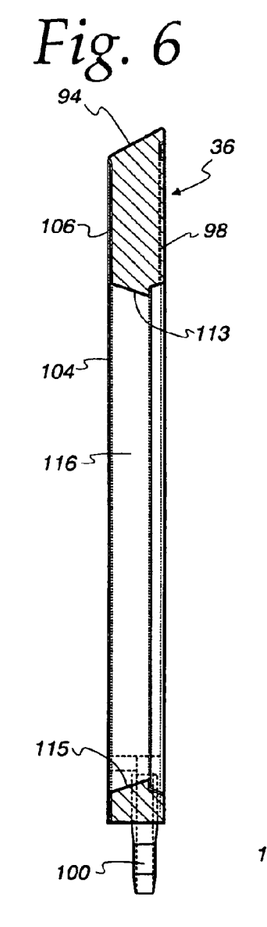
FIG. 6 is a side elevation view of the patient support table section shown in FIG. 5.
Figure 7:
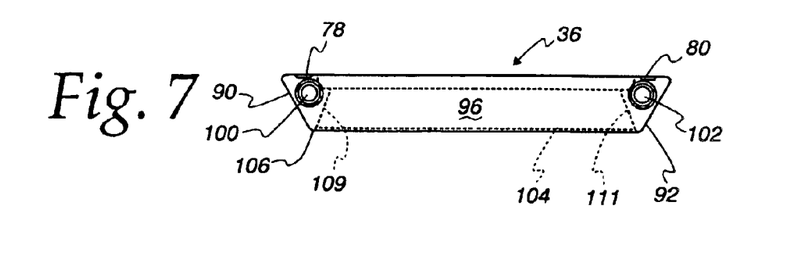
FIG. 7 is a front elevation view of the patient support table section shown in FIGS. 5 and 6.

Referring now to FIGS. 5–7, the exchangeable or upper table section 36 includes an edge 88 formed by two opposing slanted walls 90, 92, a slanted end wall 94 and an abutment wall 96 intersecting with a top surface 98. Extending from the abutment wall 96 are two fastener rods 100, 102 which are intended to be received by the fastener sleeves 69, 70, FIG. 4, of the attached or lower table section 34. The exchangeable table section also includes a bottom surface 104 having a peripheral downward projecting ridge 106, identical to the ridge 84. Like the lower section 34, the upper section 36 has the left side peripheral portion 72, the right side peripheral portion 73 and the upper peripheral portion 75. Formed in the top surface 98 is the longitudinally extending left channel 78 in the left side peripheral portion, the longitudinally extending right channel 80 in the right side peripheral portion and a laterally extending recess 112 in the upper peripheral portion 75.

As can now be appreciated, the exchangeable table section 36 is very similar to the attached table section 34 except that the exchangeable table section includes a large central opening or hole 116 through the table section, the section having slanted walls 109, 111, 113, 115 for defining the opening. This opening may contain, for example, a mesh insert to help support a portion of a patient, thereby permitting radiation therapy with a minimum amount of material interference. It is to be understood that the shape and size of the opening 116 may vary from that which is shown.

Figure 8:
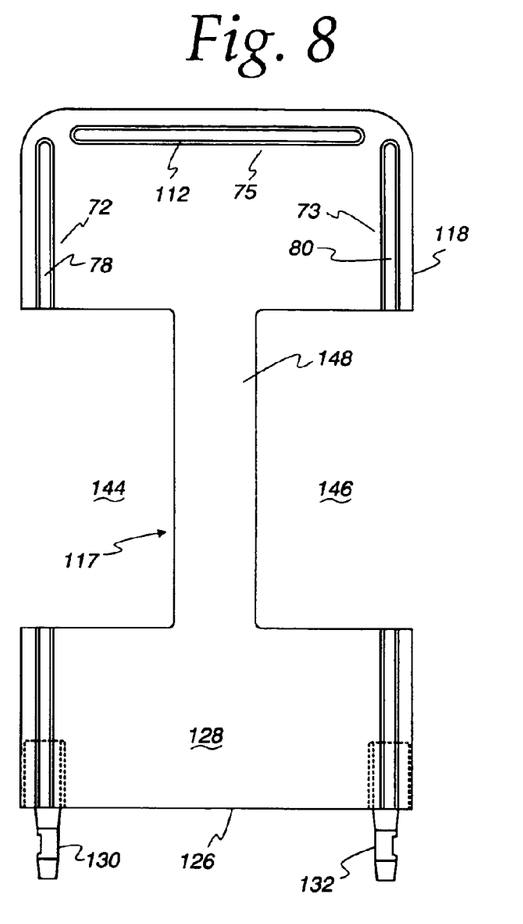
FIG. 8 is a top plan view of another version of a connectable or exchangeable upper patient support section.
Figure 9:
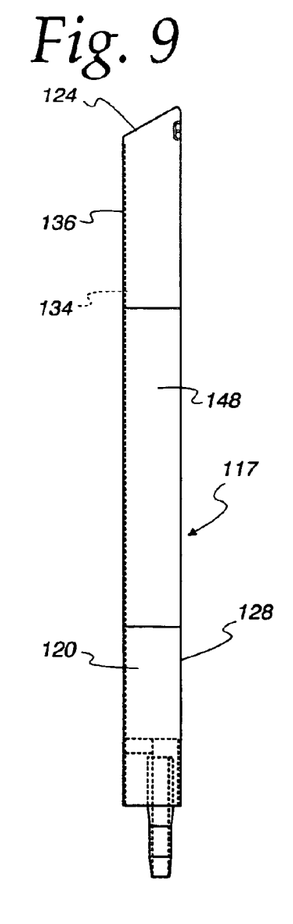
FIG. 9 is a side elevation view of the patient support table section shown in FIG. 8.
Figure 10:
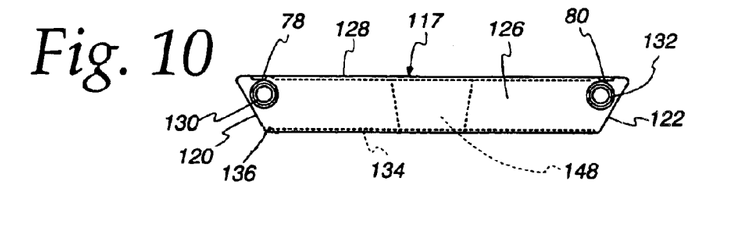
FIG. 10 is a front elevation view of the patient support table section shown in FIGS. 8 and 9.

The shape of the exchangeable table section may take other forms than that shown in FIGS. 5–7. For example, a different exchangeable table section 117 is shown in FIGS. 8–10. The exchangeable table section 117 includes an edge 118 formed by opposing slanted side walls 120, 122, a slanted end wall 124 and an abutment wall 126 intersecting a top surface 128. The table section also includes two fastener rods 130, 132, a bottom wall 134 and a bottom ridge 136. Spaced from the edge 118 are the left side peripheral portion 72, the right side peripheral portion 73 and the upper peripheral portion 75. Formed in the top surface in the respective peripheral portions is an interrupted longitudinally extending left recess or channel 78, an interrupted longitudinally extending right recess or channel 80 and a laterally extending end channel 112. The exchangeable table section 117 differs from the exchangeable table section 36 in that the table section 117 has two open regions 144, 146 into which may be placed inserts (not shown) as a function of the treatment being performed. The exchangeable table section 117 further includes a central spine 148. Having such open side regions allows for oblique radiation field. The same names and numbers are used for the peripheral portions and the channels on all embodiments because regardless of the exchangeable table section used, the peripheral portions and channels are continuations of the same elements of the attached table section.

Like the attached table section 34, the exchangeable table sections 36, 117 are made from carbon fiber and foam. The spine 148 may be made of carbon fiber without foam for added strength. Carbon fiber is very strong and yet light in weight. For example, the exchangeable section 36 may weigh only thirteen pounds. Carbon fiber also minimizes interference with radiation.

Figure 11:
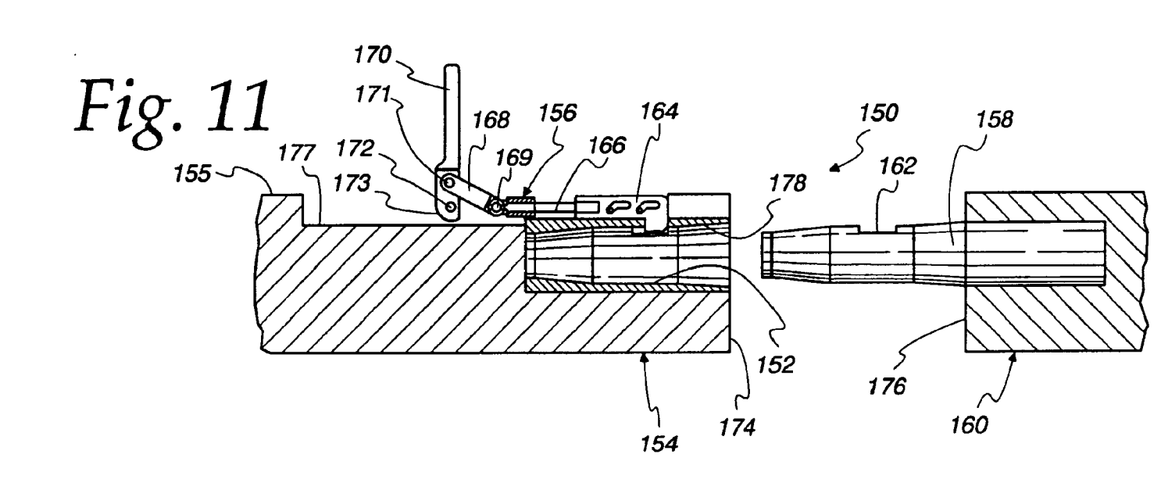
FIG. 11 is a diagrammatic section view taken along line 11, 12–11, 12 of FIG. 13 and shows a portion of the attached lower patient support table section and a portion of the exchangeable patient upper support table section in a disengaged and separated disposition.
Figure 12:
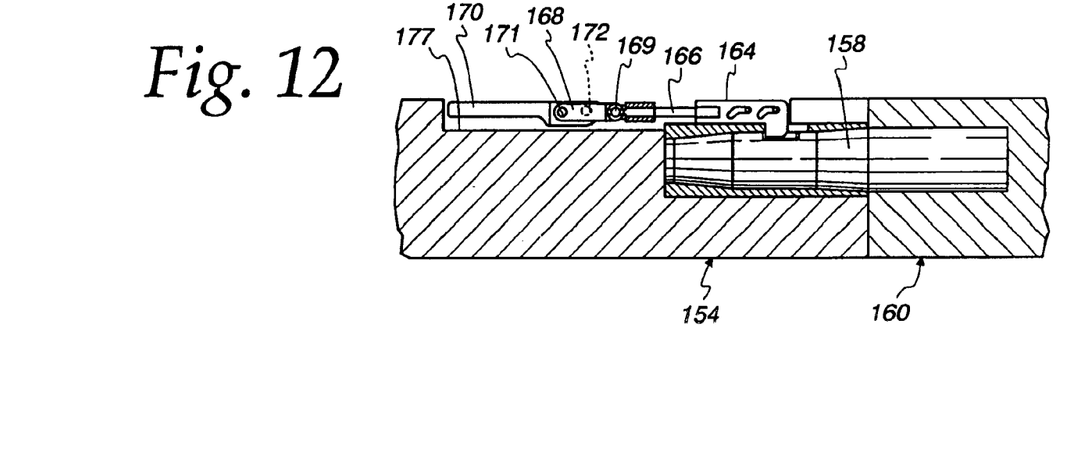
FIG. 12 is a diagrammatic section view like that of FIG. 11 but showing the lower and the upper patient support table sections in a connected locked disposition.

The ease of use and simplicity of construction of the table sections may be appreciated by referring now to FIGS. 11 and 12. In FIGS. 11 and 12, the fastener parts of the attached and exchangeable sections are illustrated in detail and show how easy it is to attach and detach the exchangeable table sections. The fastener system 150 includes a first fastener part in the form of a sleeve 152 located in an attached table section 154, and a cam-lock mechanism 156 mounted to a slanted side wall 155 of the attached table section. A second fastener part in the form of a rod 158 is attached to an exchangeable table section 160, the rod being received by the fastener sleeve 152. A notch 162 is formed in the rod 158.

The cam-lock mechanism 156 includes a latch 164 which is connected to the attached table section to be movable in a generally horizontal direction as shown in FIG. 11 with a vertical component thereby allowing the latch to lower itself so as to engage the notch 162 and to draw the rod tightly into the sleeve. The latch is connected to a first link 166 which in turn is pivotally connected to a second link 168 at a pin 169. In turn, the second link is pivotally connected to a lever handle 170 at a pin 171. The lever is also rotatably connected at a pin 172 to the attached table section and includes an eccentric surface 173 which allows the mechanism to tighten when the lever is rotated from the position shown in FIG. 11 counterclockwise to the position shown in FIG. 12. Rotating the lever around the pin 172 causes the distance between the latch and the pin 171 to increase thereby moving the latch leftwardly as well as downwardly to the position shown in FIG. 12. When this is done, an abutment wall 174 of the attached table section 154 comes into contact with an abutment wall 176 of the exchangeable table section 160. Further, when the cam-lock mechanism 156 is in a locked condition as shown in FIG. 12, the mechanism fits flush within a cavity 177 of the attached table component 154. The rod 158 may be made of any suitable material, such as aluminum. For added strength, a liner 178 of steel may be inserted into the sleeve 152.

It is understood that the cam-lock mechanism may be mounted on the exchangeable table section and the sleeve formed therein, and the rod may be fastened to the attached table section thereby reversing the arrangement shown in FIGS. 11 and 12, although such a reverse arrangement will be more expensive. It is also understood that other types of fasteners may be used to connect the attached and the exchangeable table sections together.

Figure 13:
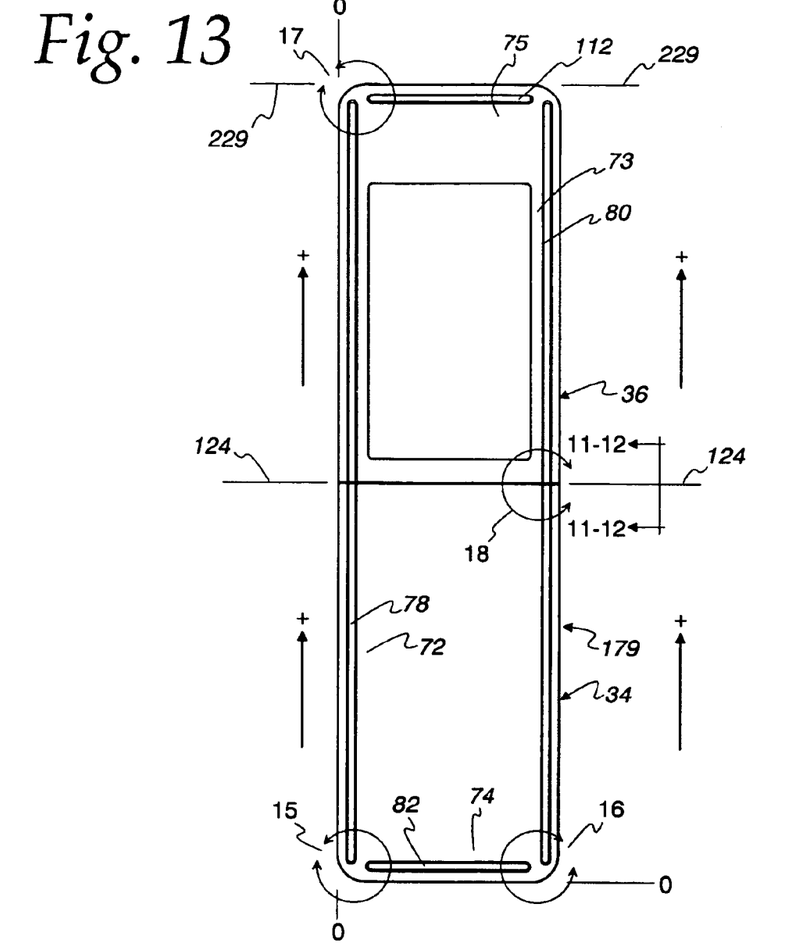
FIG. 13 is a diagrammatic plan view of the patient support table sections of FIGS. 2 and 5 and illustrating a numbering system used to provide location coordinates for the table.

Referring now to FIGS. 13–18, the table 179 of the patient support system 32 is shown fully assembled with the attached table section 34 connected to the exchangeable table section 36. As already described, the top surface of the table has right and left longitudinally channels 78, 80 and upper and lower laterally extending channels 82, 112. In the channels are location indicia in the form of scale markings, such as identical continuous sequences starting at "0" at the lower peripheral portions and extending to "229" if a centimeter scale is used. In a similar manner, the upper and lower scales 112, 82 may start at "0" at the left side of the table and continue sequentially in a positive direction, all as depicted in FIG. 13 with numbers and arrows. It is to be understood that the scales may be designated in inches or millimeters, instead of centimeters, or the scales may use any other convenient unit of measure. Also, indicia may be used where spacing is consistent but an arbitrary scale is chosen. In other words, such a number scale need not use any standard units of measure. The concept is to form a grid that may be used to accurately place a patient on the table so that the same region of the patient's body is at the same treatment location for repeated exposure to radiation, for example.

The left and right channels 78, 80 bearing location indicia are located respectively in the left and right peripheral portions 72, 73 of the table and the upper channel 112 and the lower channel 82 are located respectively at the upper peripheral portion 75 and the lower peripheral portion 74 of the table. Further, regardless of the exchangeable table section used, the scale markings will continue in sequence from those on the attached table section.

Figure 14:
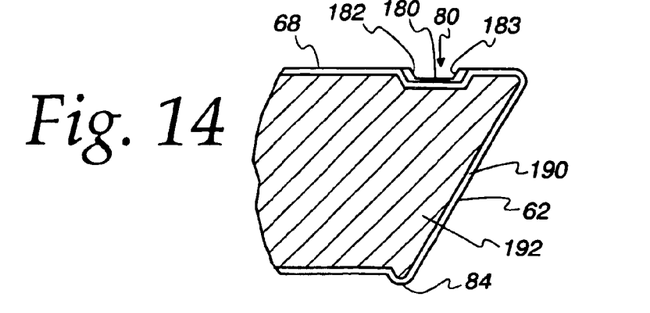
FIG. 14 is an enlarged sectional elevation view taken along line 14—14 of FIG. 2.
Figure 15:
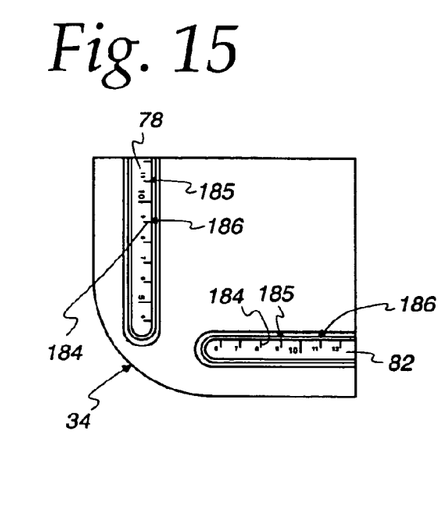
FIG. 15 is an enlarged partial plan view taken within circle 15—15 of FIG. 13.
Figure 16:
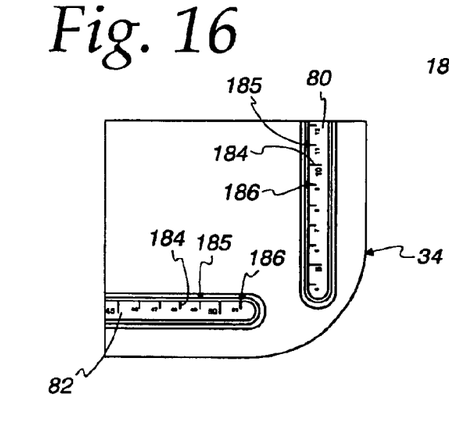
FIG. 16 is an enlarged partial plan view taken within circle 16—16 of FIG. 13.
Figure 17:
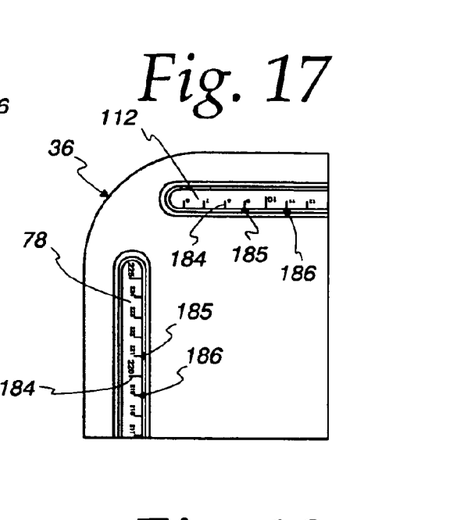
FIG. 17 is an enlarged partial plan view taken within circle 17—17 of FIG. 13.
Figure 18:
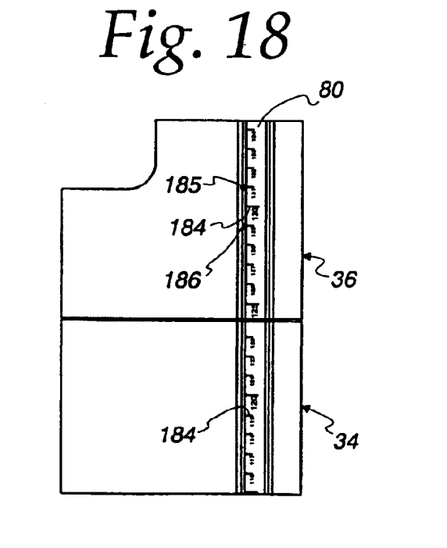
FIG. 18 is an enlarged partial plan view taken within circle 18—18 of FIG. 13.

The channels, left, right, upper and lower all include a base 180, FIG. 14, a left slanted wall 182 and a right slanted wall 183. The scale markings 184 are formed in the base 180. The channel is designed to allow easy use of the table to repeatedly located patients and to receive a clamp to allow facilitated placement of accessories. Small notches 185, 186 are formed in the left slanted wall 182 (when the slanted wall is oriented as shown in FIG. 14, otherwise the notches are located in the innermost of the slanted walls.). These notches are formed in pairs two centimeters apart and five centimeters from the next pair and may be used to receive spring biased pins or balls mounted on the clamp for locating the clamp every five centimeters.

Beneath the recess is the downwardly projecting ridge 84, FIG. 14. This element also mates with a complementing portion of a clamp. It may now be appreciated that a "C"

shaped clamp with an upper portion for engaging the base and walls of the channels and a lower portion for engaging the ridge 84 and spanning the slanted wall 62 of the table may be used to attached accessories to the table component while offering little interference with radiation treatments of a patient supported on the top surface 68 of the table. All channels and ridges are formed in the same way and also engage the clamp in the same way.

The cross section of the table sections is shown generally in FIG. 14 and include a carbon fiber skin or outer layer 190 and a foam core 192. The foam may be any suitable material, such as Rohacell Acrylic Foam. Suitable carbon fiber is 55 MSI carbon/epoxy prepreg. The carbon fiber, foam core arrangement is strong yet light weight to facilitate detaching and exchanging table sections 36. The construction also does not unduly interfere with radiation.

Referring now to FIGS. 19–23, there is illustrated a table 179 with two sections 34, 36 separated at a part line 193, an accessory clamp 200 and a bridge. The clamp includes an upper jaw portion 202 connected to a lower jaw portion 204 by a pivot shaft 206. The upper jaw 202 includes an upper arm 208 with a channel engaging finger 209. The lower jaw 204 includes a lower arm 210 with a ridge engaging groove 212. Attached to a top surface 214 of the upper arm 210 are two posts 218, 220 for engaging the bridge 222. As can seen, the bridge has post receiving openings 223, 224. The upper arm 208 also includes a scale viewing window 225. Adjacent the channel engaging finger 209 are two locator elements in the form of spring biased pins or balls 226, 227 to engage the small notches 185, 186, FIGS. 15–18.

The clamp also includes a handle 230. The clamp handle is rotatably connected to the upper jaw 202 by a bolt 231, and the handle includes a cam surface 232 which bears against a cam follower surface 234, part of the lower jaw 204. When rotating the handle from the detached or unclamped position shown in FIG. 19 to the locked or clamped position shown in FIGS. 20–23, the cam surface 232, FIG. 23, goes from a loose contact with the cam follower surface 234 to a forced bearing against the follower surface thereby tightening the lower jaw 204 of the clamp onto the ridge 84 of the table and at the same time tightening the channel engaging finger 209 of the upper jaw 202 with the channel base 182. It should be noted that the clamp will attach to the table even when the locating balls 226, 227 do not engage the small notches 185, 186.

Figure 24:
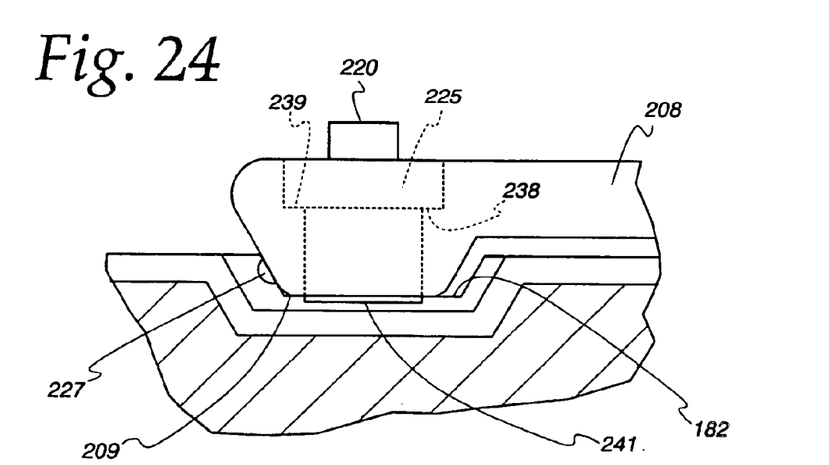
FIG. 24 is an enlarged view taken within circle 24—24 of FIG. 23.
Figure 25:
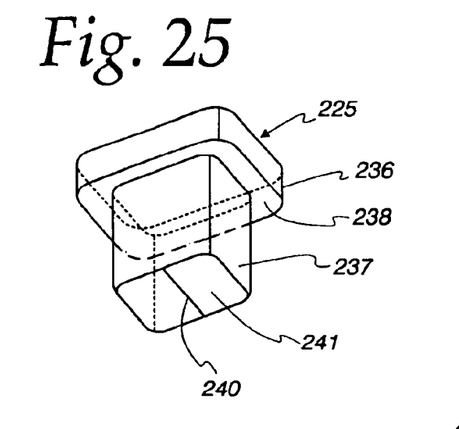
FIG. 25 is an upward looking isometric view of an indicator element with a hairline.

Referring now to FIGS. 24 and 25, the viewing window 225 is illustrated in more detail. The window includes a top portion 236 and a bottom portion 237. A shoulder 238 separates the top and bottom portions and is provided to mount on a corresponding shoulder 239 in the upper arm 208. The window also has a hairline 240 formed in a bottom surface 241. When the window is installed as shown in FIG. 24, the hairline allows an operator to move the clamp, when loose, along the scale markings to align at a precise location consistently from one treatment session to another. The window may be made from any suitable material including glass and clear plastic.

Figure 19:
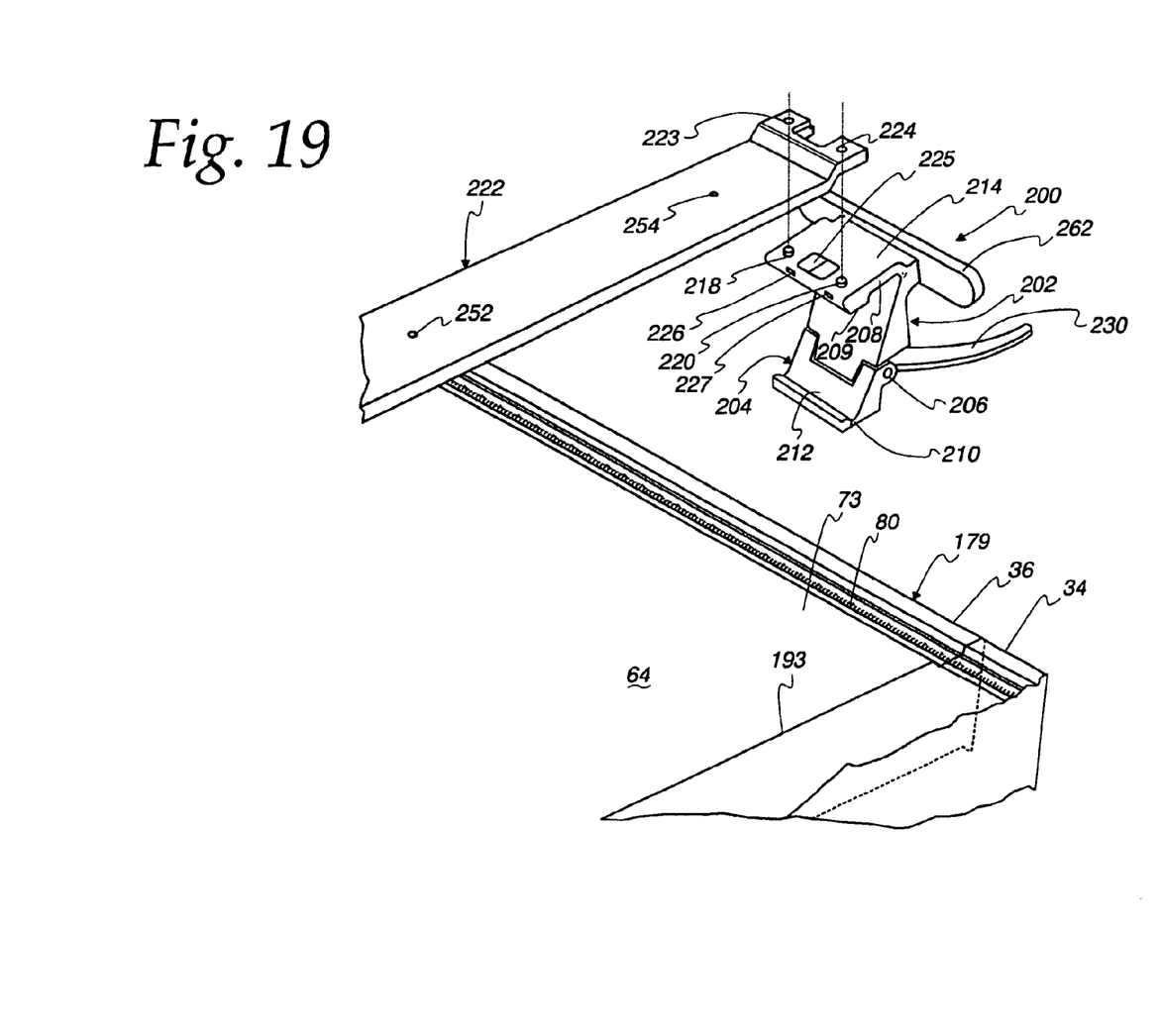
FIG. 19 is an exploded, partial isometric view of a patient support table section, a clamp and an accessory bridge.
Figure 20:
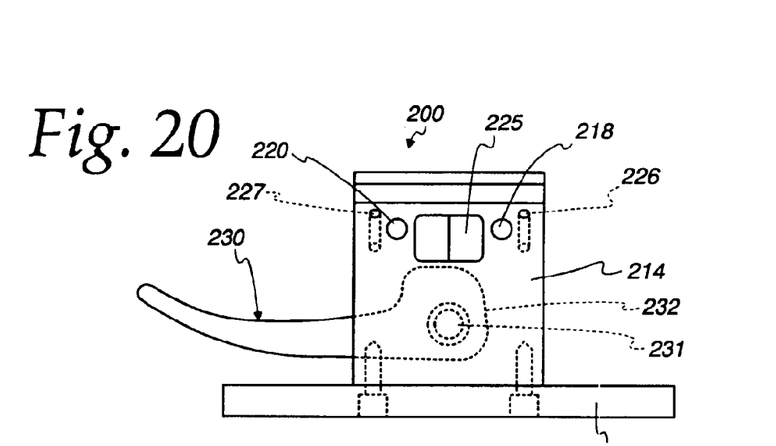
FIG. 20 is a top plan view of the clamp shown in FIG. 19.
Figure 21:
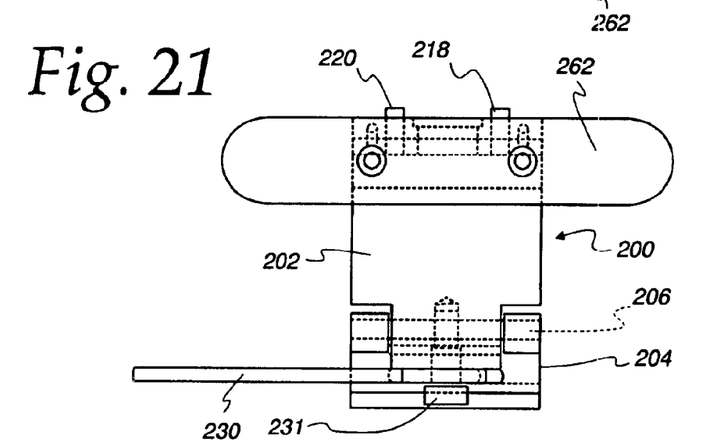
FIG. 21 is a front elevation view of the clamp shown in FIGS. 19 and 20.
Figure 22:
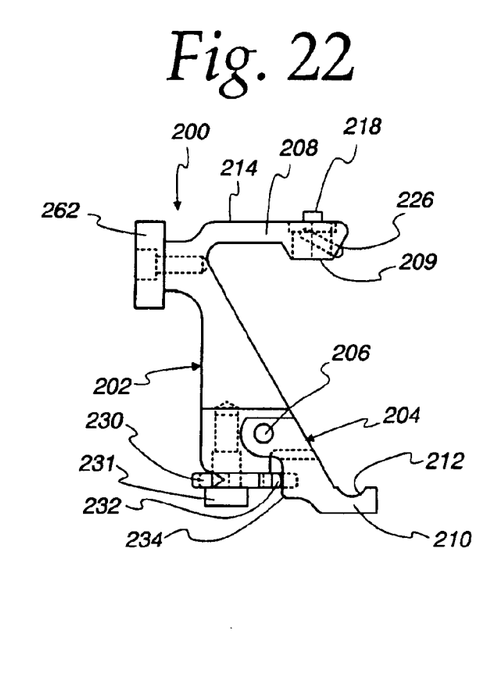
FIG. 22 is a side elevation view of the clamp shown in FIGS. 19–21.
Figure 23:
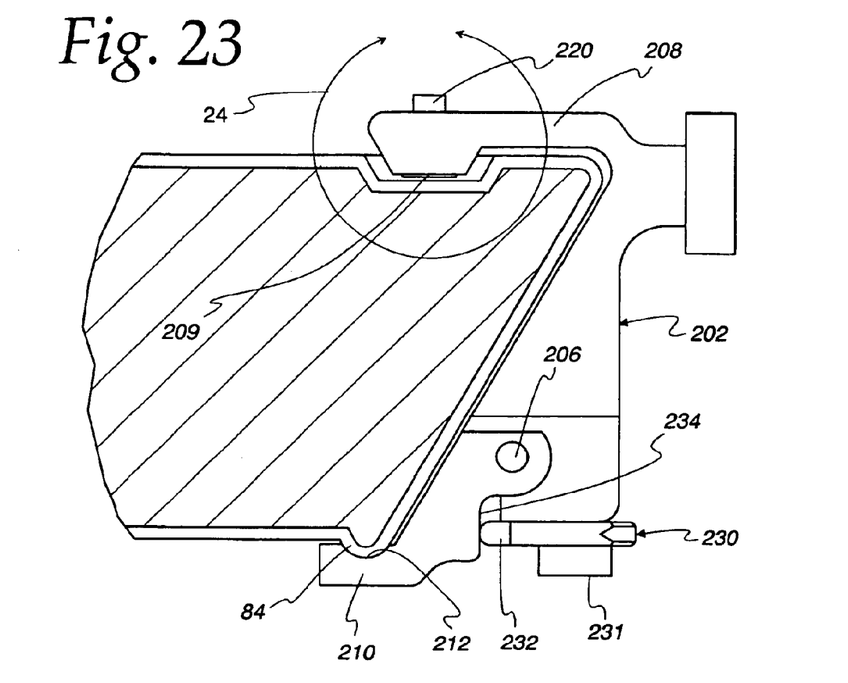
FIG. 23 is a sectional elevation view like that of FIG. 14 but including an attached clamp.
Figure 26:
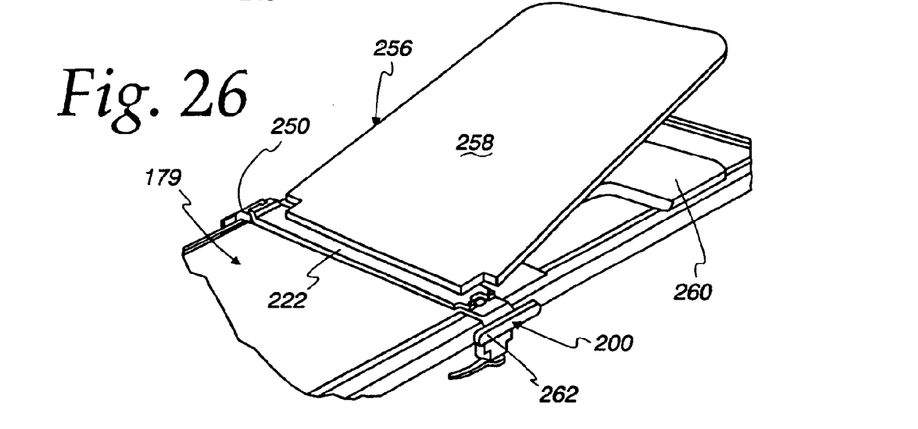
FIG. 26 is a diagrammatic isometric view of an accessory device in the form of a tilt board connected to the accessory bridge which in turn is connected to oppositely disposed clamps attached to the patient support table.

The bridge 222, FIGS. 19 and 26, extends across the top of the table components from the clamp 200 to an identical clamp 250 on the opposite side of the table 179. The bridge includes spaced openings 252, 254 which may be used to receive pins or posts from any one of a number of different accessories to enable the mounting thereof. For example, a tilt board 256 is illustrated in FIG. 26 having depending posts (not shown) that mount the board to the bridge 222. The tilt board 256 includes a back rest section 258 and a support section 260 for elevating a patient's thorax and head to a known angle. The mounting of the board relative to the table is quite easy using the hairlines on the clamps. If the bridge is to be located using the scale marking "186," these are viewed through the scale viewing window 225. The clamps can be positioned over the "186" scale marking, the bridge installed and then the board mounted. The location of the tilt board is, of course, reproducible for multiple treatments.

Figure 27:
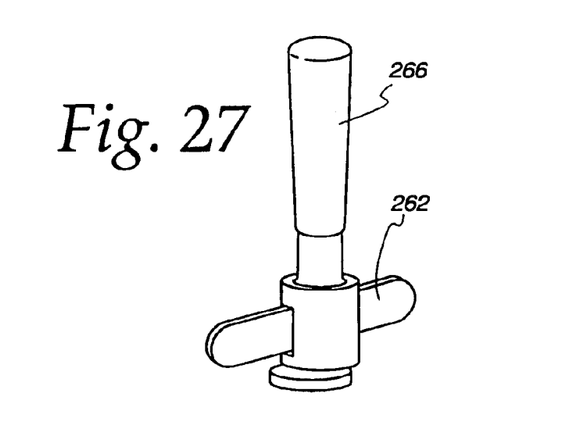
FIG. 27 is a diagrammatic isometric view of a hand grip attached to a rail of the clamp.

Each clamp also includes a support bar 262, FIGS. 19–22 and 26, to which accessories may be attached. For example, as shown in FIG. 27, a handle grip 266 is shown attached to the support bar 262. Such grips are commonly used to assist a patient when mounting or dismounting the table and to stabilize a patient's arm position during treatment.

The portions of the specification above, describes in detail preferred embodiments of the present invention. Other examples, embodiments, modifications and variations will under both the literal claim language and under the doctrine of equivalents come within the scope of the invention defined by the appended claims. For example, using different shapes for the exchangeable table sections, or different materials for the structure of the sections are all considered equivalent structures and will also come within the literal language of the claims. Still other alternatives will also be equivalent, such as different location scales or shapes of recesses and ridges, as will many new technologies. There is no desire or intention here to limit in any way the application of the doctrine of equivalents nor to limit or restrict the scope of the invention.

What is claimed is:

1. A radiotherapy treatment and imaging patient support system comprising:

a base;

a patient support table connected to said base, said table having an edge, right and left side peripheral portions, and upper and lower peripheral portions, said peripheral portions being spaced away from said edge;

location indicia formed on said table along one of said right and left peripheral portions, said indicia being a continuous sequence wherein a location on a body placed on said table is located relative to said table in a reproducible manner; and a clamp for mounting about said edge of said table, said clamp having an upper jaw portion and an opening therethrough, a lower jaw portion with an opening therethrough, a pivot shaft being operatively connected to said upper and said lower jaw portions through said openings, a lever connected to said upper jaw portion, a cam connected to said lever for bearing against said lower jaw portion, and an element having a hairline, said element being mounted in said opening in said upper jaw wherein viewing of said location indicia is facilitated.

2. The apparatus of claim 1 including:

a second location indicia mounted to said table along the other of said right and left peripheral portions, said first mentioned and said second location indicia being identical;

third and fourth location indicia mounted to said table along said upper and lower peripheral portions, said third and fourth location indicia being identical; and four longitudinally extending channels formed in said table, one channel along each of said right, said left, said upper and said lower peripheral portions, and wherein said location indicia are formed in said channels.

3. The apparatus as claimed in claim 2 wherein:

each of said channels includes two oblique side walls and a flat base, and each of said location indicia is formed on a respective base of each of said channels.

4. The apparatus as claimed in claim 3 including:

two recesses in said upper jaw portion;

two springs for mounting in said two recesses; and two locator elements for mounting in said two recesses and being biased by said two springs wherein said locator elements help locate said clamp relative to said patient support table.

5. The apparatus as claimed in claim 2 wherein:

said patient support table has first and second sections, said first section being connected to said base and said second section having a middle portion;

said middle portion includes an opening therethrough; and said middle portion includes oblique walls defining said opening.

6. The apparatus as claimed in claim 4 wherein:

said patient support table has first and second sections, said first section being connected to said base and said second section having a middle portion;

said middle portion includes an opening therethrough; and said middle portion includes oblique walls defining said opening.

7. The apparatus as claimed in claim 4 including:

two upwardly extending projections connected to said upper jaw portion; and an accessory bridge extending about the width of said table and having two openings at each end for engaging said projections connected to oppositely disposed clamps.

8. A radiotherapy treatment and imaging patient table comprising:

a patient support structure having a ton surface, a side edge, said ton surface having right and left side peripheral portions and upper and lower peripheral portions, said peripheral portions being spaced away from said edge;

location indicia formed on said support structure along one of said right and said left peripheral portions, said indicia being a continuous sequence wherein a location on a body placed on said top surface is located relative to said table in a reproducible manner; and a longitudinally extending channel formed in said top surface along one of said right and left peripheral portions; and wherein said location indicia is formed in said channel.

9. The apparatus as claimed in claim 8 wherein:

said location indicia are a series of scale markings.

10. The apparatus as claimed in claim 9 wherein:

said scale markings is sequential series of numbers.

11. The apparatus as claimed in claim 8 wherein:

said channel includes two oblique side walls and a flat base; and wherein said location indicia is formed on said base.

12. The apparatus as claimed in claim 8 including:

a second longitudinal extending channel formed in said top surface along the other of said right and left peripheral portions; and first and second lateral extending channels formed in said top surface.

13. A radiotherapy treatment and imaging patient table comprising:

a patient support structure having a top surface, a side edge, said top surface having right and left side peripheral portions and upper and lower peripheral portions, said peripheral portions being spaced away from said edge, said support structure including exchangeable sections, each of said sections having right and left peripheral portions;

location indicia formed on said support structure along one of said right and said left peripheral portions, said indicia being a continuous sequence wherein a location on a body placed on said too surface is located relative to said table in a reproducible manner; and location indicia formed on said sections wherein said location indicia of said sections continues the sequence of said first mentioned location indicia formed on said support structure.

14. The apparatus as claimed in claim 13 wherein:

one exchangeable section has a middle portion including an open therethrough.

15. The apparatus as claimed in claim 14 wherein:

said middle portion includes oblique walls defining said opening.

16. A clamp for a radiotherapy treatment and imaging patient support system comprising:

an upper jaw portion with a pivot opening and a viewing opening therethrough;

a lower jaw portion with a pivot opening therethrough;

a pivot shaft being operatively connected to said upper and said lower jaw portions through said pivot openings therethrough;

a lever connected to said upper jaw portion;

a cam connected to said lever for bearing against said lower jaw portion; and an element having a hairline, said element being mounted in said viewing opening in said upper jaw.

17. The apparatus as claimed in claim 16 including:

a surface surrounding said viewing opening in said upper jaw portion, said surface including a shoulder.

18. The apparatus as claimed in claim 17 wherein:

said element having a hairline is generally transparent and includes a shoulder for engaging said shoulder of said surface surrounding said viewing opening in said upper jaw portion.

19. The apparatus as claimed in claim 16 including:

two recesses in said upper jaw portion;

two springs mounted in said two recesses; and two locator elements mounted in said two recesses wherein said locator elements help locate said clamp relative to a patient support table.

20. The apparatus as claimed in claim 19 wherein:

each of said locator elements is a pin.

* * * * *